United States Patent
Plotnikov et al.

(10) Patent No.: US 7,402,999 B2
(45) Date of Patent: Jul. 22, 2008

(54) PULSED EDDY CURRENT PIPELINE INSPECTION SYSTEM AND METHOD

(75) Inventors: Yuri Plotnikov, Niskayuna, NY (US);
Andrew May, Schenectady, NY (US);
Shridhar Nath, Niskayuna, NY (US);
Changting Wang, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 90 days.

(21) Appl. No.: 11/290,916

(22) Filed: Nov. 30, 2005

(65) Prior Publication Data

US 2007/0120559 A1    May 31, 2007

(51) Int. Cl.
*G01N 27/72* (2006.01)
(52) U.S. Cl. ...................................... 324/220
(58) Field of Classification Search ......... 324/219–221, 324/228, 237, 238, 240–243, 262
See application file for complete search history.

(56) References Cited

U.S. PATENT DOCUMENTS

| | | | |
|---|---|---|---|
| 3,225,293 A | 12/1965 | Wood et al. | |
| 3,483,466 A | 12/1969 | Crouch et al. | |
| 3,539,915 A * | 11/1970 | Wood et al. | 324/220 |
| 3,967,194 A * | 6/1976 | Beaver et al. | 324/220 |
| 4,675,604 A * | 6/1987 | Moyer et al. | 324/220 |
| 4,769,598 A | 9/1988 | Krieg et al. | |
| 4,808,924 A * | 2/1989 | Cecco et al. | 324/220 |
| 5,313,838 A * | 5/1994 | Gondard et al. | 73/623 |
| 5,506,503 A * | 4/1996 | Cecco et al. | 324/220 |
| 5,565,633 A * | 10/1996 | Wernicke | 73/865.8 |
| 5,623,203 A * | 4/1997 | Hosohara et al. | 324/220 |
| 5,747,998 A * | 5/1998 | Fowler et al. | 324/263 |
| 6,232,773 B1 * | 5/2001 | Jacobs et al. | 324/220 |
| 6,414,483 B1 | 7/2002 | Nath et al. | 324/232 |
| 6,429,759 B1 | 8/2002 | Schlitz et al. | 335/16 |
| 6,545,469 B1 | 4/2003 | Batzinger et al. | 324/238 |
| 6,670,808 B2 | 12/2003 | Nath et al. | 324/230 |
| 6,707,297 B2 | 3/2004 | Nath et al. | 324/240 |
| 6,720,775 B2 * | 4/2004 | Plotnikov et al. | 324/529 |
| 6,794,963 B2 | 9/2004 | O'Keeffe et al. | 335/21 |
| 6,812,697 B2 | 11/2004 | McKnight et al. | 324/262 |
| 6,847,207 B1 * | 1/2005 | Veach et al. | 324/220 |
| 6,888,347 B2 | 5/2005 | Batzinger et al. | 324/242 |
| 6,892,115 B2 | 5/2005 | Berkcan et al. | 700/286 |

(Continued)

FOREIGN PATENT DOCUMENTS

DE    19746511 A1    4/1999

(Continued)

*Primary Examiner*—Jay M Patidar
(74) *Attorney, Agent, or Firm*—Fletcher Yoder

(57) ABSTRACT

A pulsed eddy current pipeline inspection device is provided. The pulsed eddy current pipeline inspection device comprises a plurality of stages longitudinally spaced apart from each other and adapted to move between a contracted position and an expanded position, and a plurality of sensors disposed around at least a portion of a circumference of each of the plurality of stages in the contracted position with at least one gap between sensors in each of the plurality of stages in the expanded position, the plurality of sensors being arranged such that the at least one gap in a first one of the plurality of stages is aligned with a portion of a second one of the plurality of stages that has sensors disposed thereon.

22 Claims, 5 Drawing Sheets

U.S. PATENT DOCUMENTS

| | | |
|---|---|---|
| 6,911,826 B2 | 6/2005 | Plotnikov et al. ............ 324/529 |
| 6,922,641 B2 | 7/2005 | Batzinger et al. ............. 702/35 |
| 2003/0193331 A1 | 10/2003 | Nath et al. .................. 324/240 |
| 2003/0222509 A1 | 12/2003 | Andarawis et al. .......... 307/139 |
| 2004/0024475 A1 | 2/2004 | Berkcan et al. ................ 700/22 |
| 2004/0056656 A1 | 3/2004 | McKnight et al. ........... 324/262 |
| 2005/0057247 A1 | 3/2005 | Batzinger et al. ........... 324/243 |

FOREIGN PATENT DOCUMENTS

| | | |
|---|---|---|
| DE | 10300383 A1 | 7/2004 |
| EP | 1267161 A2 | 12/2002 |
| GB | 2219975 A | 2/1996 |
| WO | WO95/00840 | 1/1995 |

\* cited by examiner

PULSED EDDY CURRENT PIPELINE INSPECTION SYSTEM AND METHOD

BACKGROUND

This invention relates generally to non-destructive evaluation of pipelines and more particularly to a method and apparatus for inspecting electrically conductive structures using pulsed eddy current.

Pipelines are widely used in a variety of industries, allowing a large amount of material to be transported from one place to another. A variety of fluids such as oil and/or gas are transported cheaply and efficiently using pipelines. Particulate matter, and other small solids suspended in fluids may also be transported through pipelines. Underground and underwater (deep sea) pipelines typically carry enormous quantities of oil and gas products that are important to energy-related industries, often under high pressure and at extreme temperatures and at high flow rates.

Flaws in constituent pipes may cause pipeline integrity degradation as the pipeline infrastructure ages. Corrosion of a pipeline can be caused by small spots of weakness, subsidence of the soil, local construction projects, seismic activity, weather, and simply wear and tear caused by normal use, and can lead to defects and anomalies in the pipeline. Thus, flaws or defects and anomalies can appear in the surface of the pipeline in the form of corrosion, mechanical damage, fatigue, crack, stress, corrosion cracks, hydrogen induced cracks, or distortion attributable to dents or wrinkles.

Maintaining and protecting existing pipeline networks is proving to be a challenge. Current state-of-art inline inspection systems employ devices known as pipeline inspection gages (PIGs) to traverse sections of pipe in situ and provide data that may be evaluated to identify structural defects. Such PIGs acquire data from multiple sensors while traveling inside the pipeline. A typical single run for the PIG may be more than 100 km long. The use of PIGs allows evaluation of the integrity of a pipeline section without costly excavation and insulation removal to get access to the outer wall and conduct nondestructive inspection of the pipeline section.

PIGs may employ a wide range of sensor technology to collect information about pipelines. Examples of technologies that may be used include magnetic flux leakage (MFL), ultrasound (UT) or eddy current (EC). Each of these methodologies has its limitations. For instance, MFL systems rely on high field permanent magnets, which are bulky, heavy and have significant dragging force. As a result, PIGs employing MFL technology are suitable for inspecting pipelines that have relatively smooth bends. The UT method requires mechanical coupling with pipe walls and is not suitable for gas pipes or contaminated walls. Existing EC pigs are typically employed to inspect non-magnetic metal piping. In carbon steel pipes, the depth of penetration is of eddy currents is relatively small because of magnetic permeability which leads to a low frequency solution using large inductive coils for deep penetration and large area integration to prevent local variations of magnetic permeability. The need for deep magnetic penetration and large area integration makes EC pigs not suitable for restrictive pipeline environments that have relatively sharp bends.

Remote field EC and transient EC technologies have been developed to overcome some of the aforementioned problems. However, remote field EC and transient EC technologies do not facilitate the inspection of large diameter, thick carbon steel pipelines with high spatial resolution to detect areas of pitting corrosion with a moving PIG. Since remote EC systems use a spatial separation between exciting and sensing elements, large areas adjacent to sharp turns and valves are left uninspected. Additionally, remote field EC and transient EC technologies do not facilitate low power consumption for automatic PIGs. A PIG adapted to facilitate internal inspection of pipelines that have sharp turns and valves with reduced clearance is desirable.

BRIEF DESCRIPTION

Briefly, in accordance with one exemplary embodiment of the present invention, a pulsed eddy current pipeline inspection device is provided. The pulsed eddy current pipeline inspection device comprises a plurality of stages longitudinally spaced apart from each other and adapted to move between a contracted position and an expanded position, and a plurality of sensors disposed around at least a portion of a circumference of each of the plurality of stages in the contracted position with at least one gap between sensors in each of the plurality of stages in the expanded position, the plurality of sensors being arranged such that the at least one gap in a first one of the plurality of stages is aligned with a portion of a second one of the plurality of stages that has sensors disposed thereon.

A method of evaluating a pipeline is also disclosed. An exemplary embodiment of that method comprises driving a pulsed eddy current measuring device through the pipeline, the pulsed eddy current measuring device comprising a plurality of stages, each of the plurality of stages adapted to move between a contracted position in which a plurality of sensors are disposed around at least a portion of a circumference of each of the plurality of stages with no gap therebetween and an expanded position in which at least one gap exists between sensors disposed on each of the plurality of stages, the plurality of sensors being arranged such that the gap between sensors disposed around a first one of the plurality of stages in the expanded position is coincident with and longitudinally spaced apart from a location of at least a portion of the plurality of sensors around at least a second one of the plurality of stages, and placing the pulsed eddy current measuring device in the contracted position to navigate a constricted portion of the pipeline.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Exemplary embodiments of the present invention relate to the examination of the efficacy of pipelines. In particular, a pipeline inspection gage (PIG) comprises a plurality of sensor stages, each of which comprises a plurality of sensor sectors. The PIG employs pulsed eddy current (PEC) technology to obtain information from the sensors about possible defects in or degradation of the wall of the pipeline. As explained below, the use of PEC technology allows the sensors to be disposed in such a manner that the PIG may be placed in either a contracted position or an expanded position. In the contracted position, the PIG may be able to traverse relatively sharp bends in the pipeline.

Figure 1:
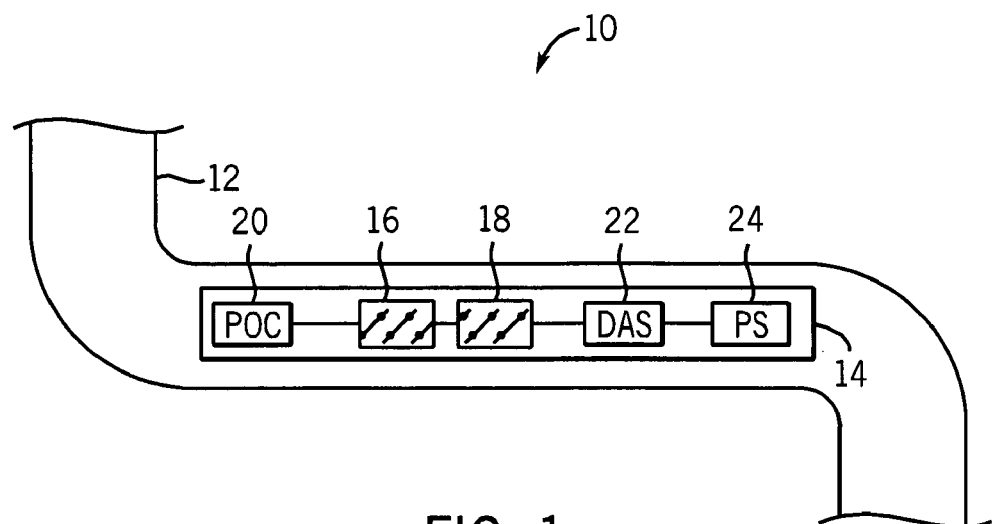
FIG. 1 is a block diagram showing a pipeline inspection system according to an exemplary embodiment of the present invention.

FIG. 1 is a diagrammatic representation of a pipeline inspection system, designated generally by reference numeral 10. The pipeline inspection system 10, which is adapted to inspect a pipeline 12, comprises a pipeline inspection gage (PIG) 14. The PIG 14 is a scanning device placed inside the pipeline and is used to gather data about the walls of the pipeline 12. The data may be analyzed to identify potential flaws such as weak spots and the like in the pipeline walls. The PIG 14 may be transported through the length of the pipeline with the fluid flow in the pipeline. In the exemplary embodiment illustrated in FIG. 1, the PIG 14 employs pulsed eddy current (PEC) sensors or probes to obtain data about the walls of the pipeline 12.

The PIG 14 comprises a first sensor stage 16 and a second sensor stage 18. The first sensor stage 16 and the second sensor stage 18 are constructed such that each has an expanded position and a contracted position. In the contracted position, the first sensor stage 16 and the second sensor stage 18 may be sufficiently small in diameter to allow the PIG 14 to traverse relatively sharp bends within the pipeline 12 compared to pipeline obstacles that may be traversed when the sensor stages 16, 18 are in the expanded position.

In the embodiment illustrated in FIG. 1, the PIG 14 additionally comprises a positional component (POC) 20, which determines the position and orientation of PIG 14 in the pipeline 12. The PIG 14 further includes a data acquisition system (DAS) 22 for receiving the data acquired by the first sensor stage 16 and the second sensor stage 18. A power source (PS) 24 provides power to the first sensor stage 16, the second sensor stage 18, the POC 20 and the DAS 22, as well as other associated components of the PIG 14. Those of ordinary skill in the art will appreciate that the PIG 14 may additionally comprise additional components such as an onboard clock for time stamping each record as acquired by the DAS 22 or the like. Similarly, the pipeline inspection system 10 may include additional components like magnetometers or magloggers, odometers and an off-board clock to record position and the overall distance traveled by the PIG 14.

Figure 2:
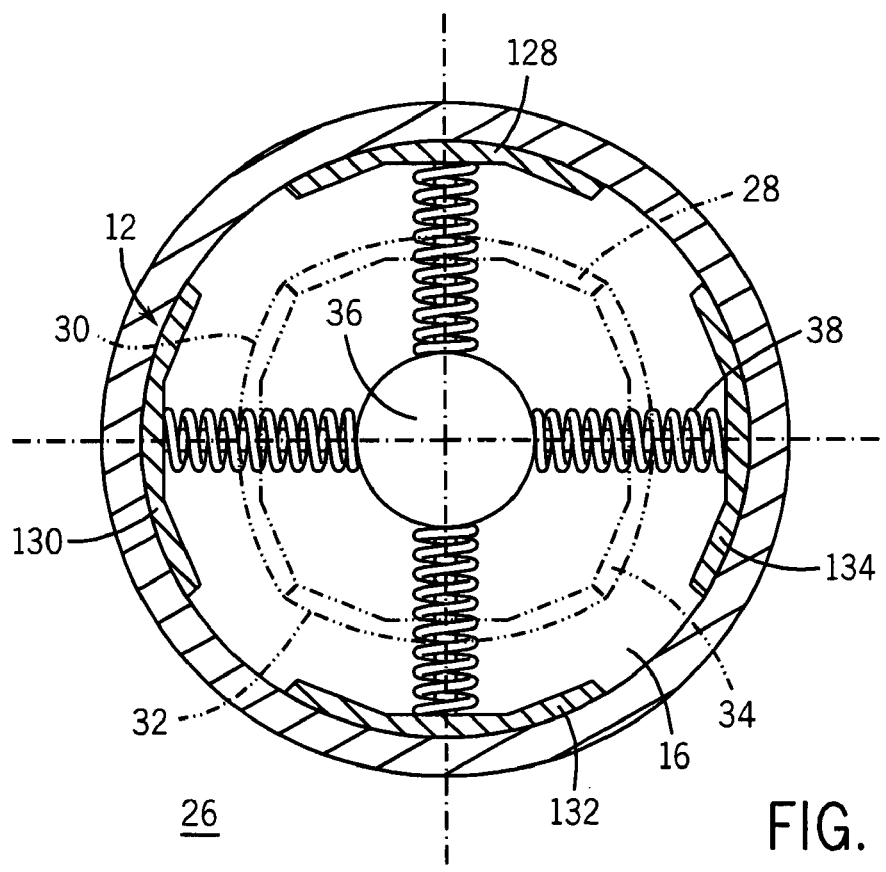
FIG. 2 is a cross-sectional view of a pipeline inspection gage (PIG) according to an exemplary embodiment of the present invention.

FIG. 2 is a cross-sectional view through a central axis 36 of the PIG 14 illustrated in FIG. 1. The figure is generally referred to by the reference numeral 26. The cross-section view illustrated in FIG. 2 shows the operation of one of the sensor stages illustrated in FIG. 1. For purposes of illustration, the first sensor stage 16 (FIG. 1) is illustrated in FIG. 2. The first sensor stage 16 comprises a plurality of sensor sectors 28, 30, 32, and 34. The sensor sectors 28, 30, 32 and 34 are illustrated in FIG. 2 in phantom lines in a contracted position. The same sensor sectors are respectively labeled as 128, 130, 132 and 134, which are shown in an expanded position relative to the central axis 36.

Each of the plurality of sensor sectors 28, 30, 32 and 34 is attached to an expansion mechanism 38, which may comprise a spring, a hydraulic system or the like, to drive the respective sensor sector between the contracted position and the expanded position. In the contracted position, the PIG 14 may have a diameter of about 60%-70% of its value relative to the expanded position. By moving the sensor stages 16, 18 to the contracted position, the PIG 14 may be able to effectively travel through relatively sharp bends or other obstacles in pipeline the pipeline 12.

Figure 3:
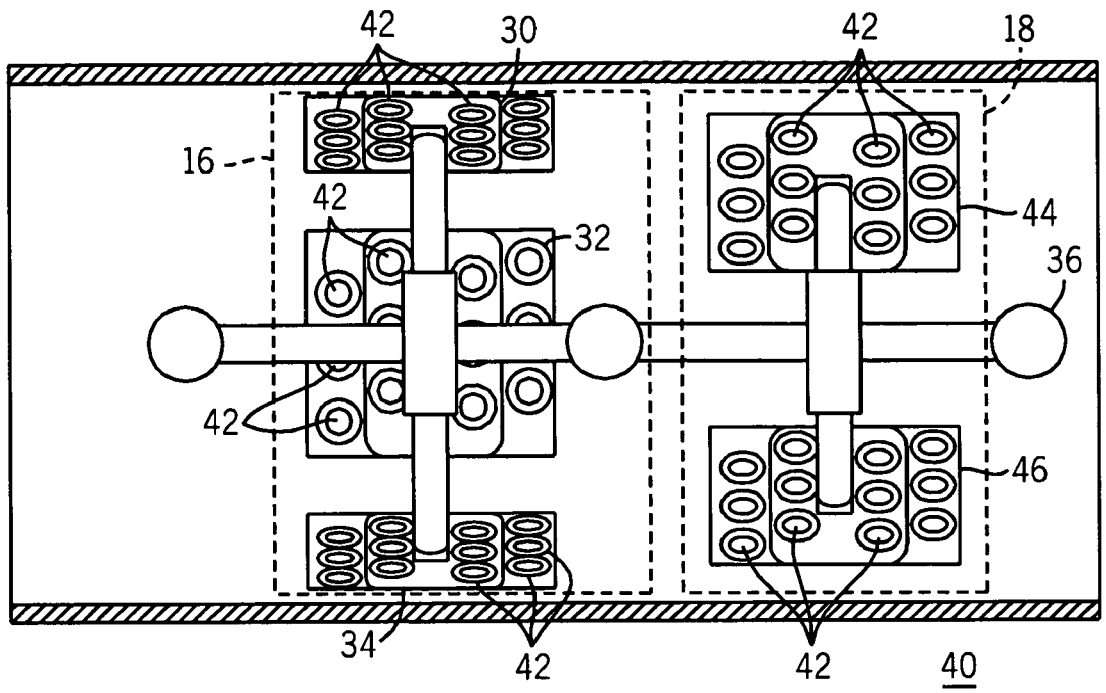
FIG. 3 is a diagram of a multi-stage PIG according to an exemplary embodiment of the present invention.

FIG. 3 is a diagram showing the sensor stages 16, 18 of a multi-stage PIG 14, as illustrated in FIG. 1. The figure is generally referred to by the reference numeral 40. The first sensor stage 16 and the second sensor stage 18 are shown in FIG. 3 in dash lines. The first sensor stage 16 comprises sensor sectors 30, 32, and 34. Each of the sensor sectors 30, 32, and 34 comprises a plurality of sensors 42, which may also be referred to as receivers herein. Similarly, the second sensor stage 18 comprises a sensor stage 44 and a sensor stage 46. The sensor stages 44, 46 each comprise a plurality of receivers 42. In an exemplary embodiment, the sensors are disposed on the sensor sectors of the first sensor stage 16 and the second sensor stage 18 such that the first sensor stage 16 and the second sensor stage 18 are each able to have complete circumferential coverage of a pipeline when the sensor stages are in the expanded position. In addition, the placement of the sensor sectors 44, 46 relative to the sensor sectors 30, 32 and 34 may be made such that the sensor sectors 44 and 46 of the second sensor stage 18 cover a circumferential position corresponding to the gaps between the sensor sectors 30, 32 and 34 of the first sensor stage 16 when both sensor stages are in the expanded position. In this manner, complete circumferential coverage of the pipeline 12 may be obtained when the sensor stages 16, 18 are in the expanded position.

The PIG 14 (FIG. 1) is desirably adapted to employ pulsed eddy current (PEC) technology to obtain data about the pipeline 12 via the sensors. In a PEC system, PEC signals are sent toward the walls of the pipeline 12 and reflected signals are received and measured. PEC technology is different from remote eddy current technology. In a remote eddy current system, a drive coil is excited with a sinusoidal current input. For effective results, the drive coil must be physically separated from the sensors by a relatively large distance to facilitate reception of a returned signal from the pipeline being examined.

In contrast, a PEC system replaces the sinusoidal input waveform with a sequence of pulsed current excitation waveforms. The drive coil is excited during an initial pulse. The current is then allowed to stabilize. Return signals reach the sensors during the stable period. In this manner, relatively small changes correlative to potential damage in the pipeline 12 may be observed. Moreover, the PIG 14 may be made more compact in a PEC system because the drive coil may be more closely located to the receiving sensors. In an exemplary embodiment, the drive coil may be disposed adjacent to one or more of the receiving sensors.

For purposes of clarity, only three sensor sectors are illustrated in FIG. 3 for the first sensor stage 16 and two sensor sectors are illustrated for the second sensor stage 18. Those of ordinary skill in the art will appreciate that the specific number of sensor sectors per sensor stage is not an essential aspect of the present invention. Moreover, the number of sensor sectors may be chosen based on a variety of design considerations, including having a sufficient number of sensor sectors in the second sensor stage to correspond to the number of gaps between the sensor sectors in the first sensor stage when the sensor stages are in the expanded position.

During inspection of a pipeline, the arrangement of sensors described above yields uniform surface coverage. By way of example, if there are four sectors in each stage of a PIG, the diameter may be thought of as divided by four pitch in the circumferential direction between sensor sectors. A 300 mm internal diameter pipeline may require a total of 192 pick-up sensors or transducers to acquire transient responses from the wall of a pipeline having a 4.9 mm pitch in the circumferential direction. Continuing to assume two sensor stages and four sensor sectors per stage, each sector may have 24 sensors arranged into four linear arrays of six sensors located at a spatial grid with 19.6 mm step. The linear arrays may be sequentially shifted in a circumferential direction by 4.9 mm to provide complete surface coverage of the pipeline 12 with a 4.9 mm grid.

A combination of a large area drive coil and relatively small pick-up sensors may allow high resolution eddy current imaging of the wall of the pipeline 12. In the described example, the system may need only a single drive pulse to excite simultaneously all eight drive coils. The sensors may be placed as close to the drive coil windings as possible to facilitate measurement of the transient response to the eddy current induced only by the adjacent drive coil.

Figure 4:
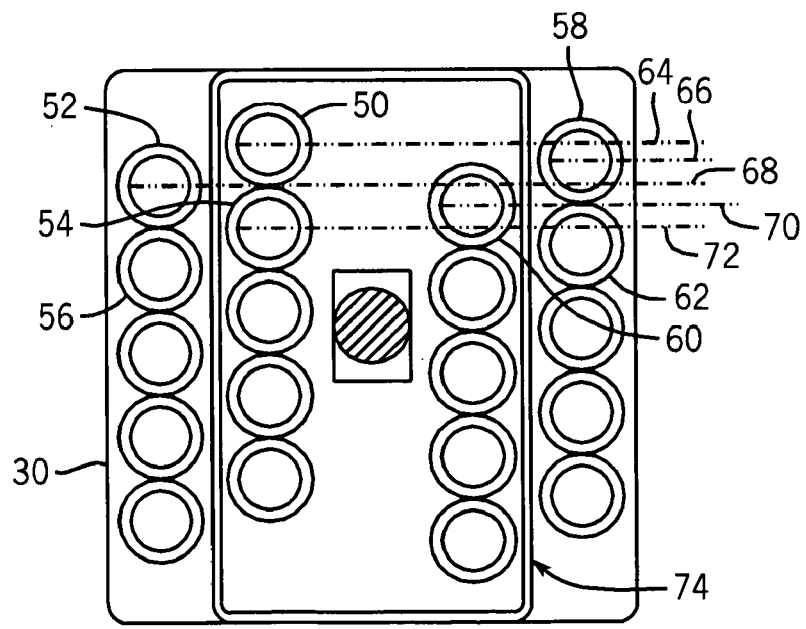
FIG. 4 is a diagram of a sensor sector of a multi-stage PIG according to an exemplary embodiment of the present invention.

FIG. 4 is a diagram of a sensor sector of a multi-stage PIG according to an exemplary embodiment of the present invention. The figure is generally represented by the reference numeral 48. FIG. 4 represents an exemplary embodiment that may be employed for each of the sensor sectors illustrated in FIG. 3. For purposes of illustration, the sensor sector 30 of the first sensor stage 16 is illustrated in FIG. 4. The sensor sector 30 employs a drive coil 74 to excite the respective sensors. The drive coil is used to inject transient magnetic flux into the wall of the pipeline 12. As explained below with reference to FIG. 5, a square pulse of electrical current from a pulser (see FIG. 6) is desirably employed.

The sensor sector 30 comprises a plurality of transducers 50, 52, 54, 56, 58 and 60 arranged into vertical linear arrays, as illustrated in FIG. 4. Each of the transducers 50, 52, 54, 56, 58 and 60 are given their own reference number in FIG. 4, but they generally correspond to the sensors 42 illustrated in FIG. 3. By way of example, the sensor sector 30 is illustrated in FIG. 4, but other sensor sectors of a given sensor stage may be arranged in a similar manner. The linear arrays formed by the transducers 50, 52, 54, 56 and 58 are offset relative to each other by fourths of the diameter of the transducers. By way of explanation, the transducers are disposed so that a center line 64 through the transducer 50 (of the second linear array from the left) runs through the transducer 58 (of the fourth and final linear array from the left) at about a quarter of the diameter from the top of the sensor 58. A centerline 68 drawn with reference to the sensor 52 (of the first linear array on the left) runs through the transducer 58 at about a quarter of the way from the bottom of the sensor 58. A centerline 70 extending through the transducer 60 (of the third linear array on the left) runs between the sensor 58 and the sensor 62. Lastly, a centerline 72 extending through the center of the transducer 54 and strikes the sensor 62 at about one-quarter from the top of the sensor 62. The exemplary sensor arrangement illustrated in FIG. 4 provides overlapping coverage of the pipeline 12.

Figure 5:
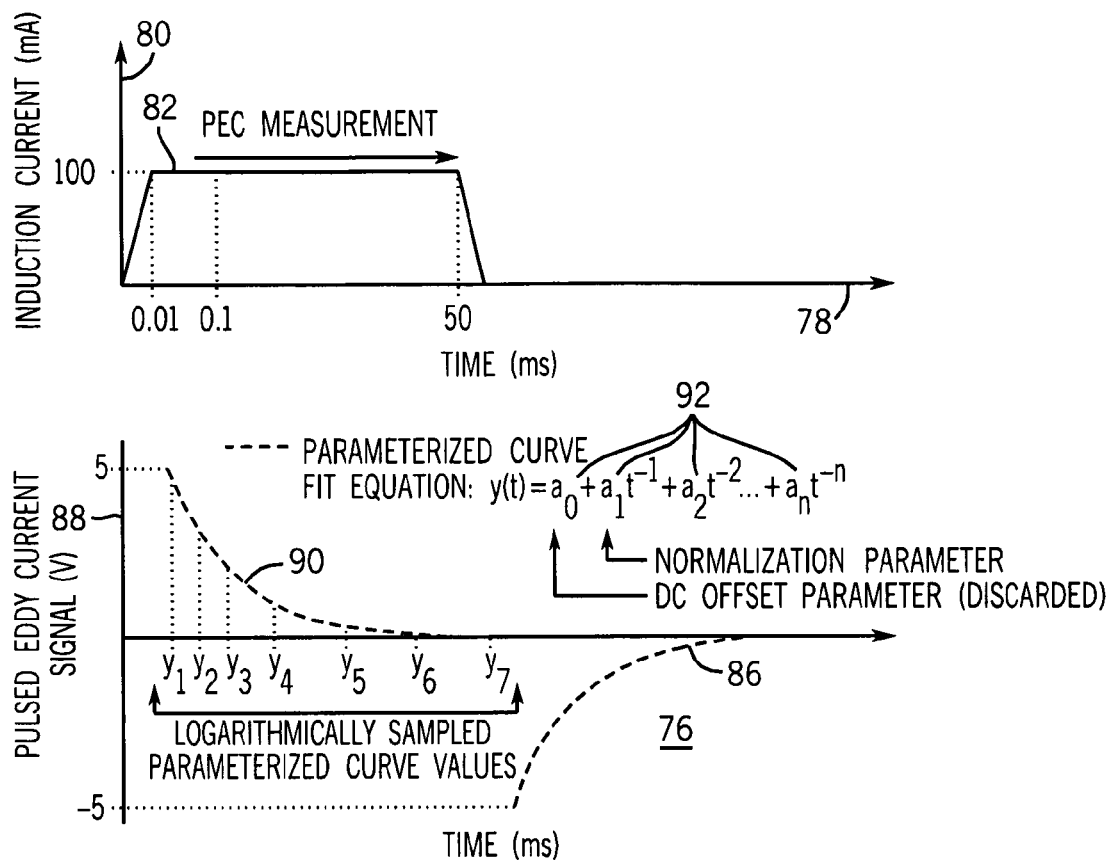
FIG. 5 is a graphical representation of pulsed eddy current (PEC) signals useful in explaining the operation of a PIG according to an exemplary embodiment of the present invention.

FIG. 5 is a graphical representation useful in explaining the operation of the PEC technology employed by the PIG 14 (FIG. 1). The graph is generally identified by the reference numeral 76. An x-axis 78 located in the upper portion of the graph 76 corresponds to time in milliseconds. A y-axis 80 located in the upper portion of the graph 76 corresponds to an induction current through a drive coil such as the drive coil 74 (FIG. 4). A PEC induction current waveform 82 is graphically represented relative to the x-axis 78 and the y-axis 80. As illustrated in FIG. 5, the induction current indicated rises quickly over about 0.01 ms to a relatively stable level lasting from about 0.01 ms until about 50 ms. Thereafter, the current drops precipitously.

The bottom portion of FIG. 5 illustrates a corresponding voltage signal induced in pick-up sensors such as the transducers 52, 54, 56, 58, 60 and 62 illustrated in FIG. 4. With respect to the bottom portion of the graph, an x-axis 86 corresponds to time in milliseconds. A y-axis 88 corresponds to a signal voltage. A sensor voltage waveform 90 illustrates the corresponding sensor voltage relative to the induction current waveform of the top portion of the graph illustrated in FIG. 5. As shown, the voltage level of the sensor voltage waveform 90 is relatively high as the induction current 82 rapidly increases. Thereafter, the value of the voltage signal 90 decays slowly while the current illustrated by the PEC induction current waveform 82 remains stable. The value of the sensor voltage waveform 90 at various times may correspond to damage of the pipeline 12 because the signal received by the transducers may be affected by damaged areas of the pipeline. By measuring the value of the sensor voltage waveform 90 at various times, a mathematical model of the efficacy of a pipeline such as the pipeline 12 may be created. As illustrated in FIG. 5, a parameterized curve fit equation may be developed based on measurements of the sensor voltage waveform 90. A plurality of parametric coefficients 92 corresponding to the sensor voltage waveform 90 may be determined and stored during a measurement operation. Moreover, by storing only the coefficients in an on-board memory of the PIG 14, data corresponding to a representation of an extended section of the pipeline 12 may be economically preserved for later evaluation. The parametric coefficients 92 may be later used to reconstruct the sensor voltage waveform 90 to identify potential anomalies in the surface of the pipeline 12.

To determine the parametric coefficients 92 representative of the condition of the pipeline, a compression routine may be applied to the actual value obtained for the sensor voltage waveform 90. This form of parameterization is believed to provide a basis for sufficient evaluation of the walls of the pipeline 12 under a typical range of sensor lift-off, sample permeability, conductivity and thickness conditions expected during normal operation of a pulse eddy current sensor for its intended operation.

Figure 6:
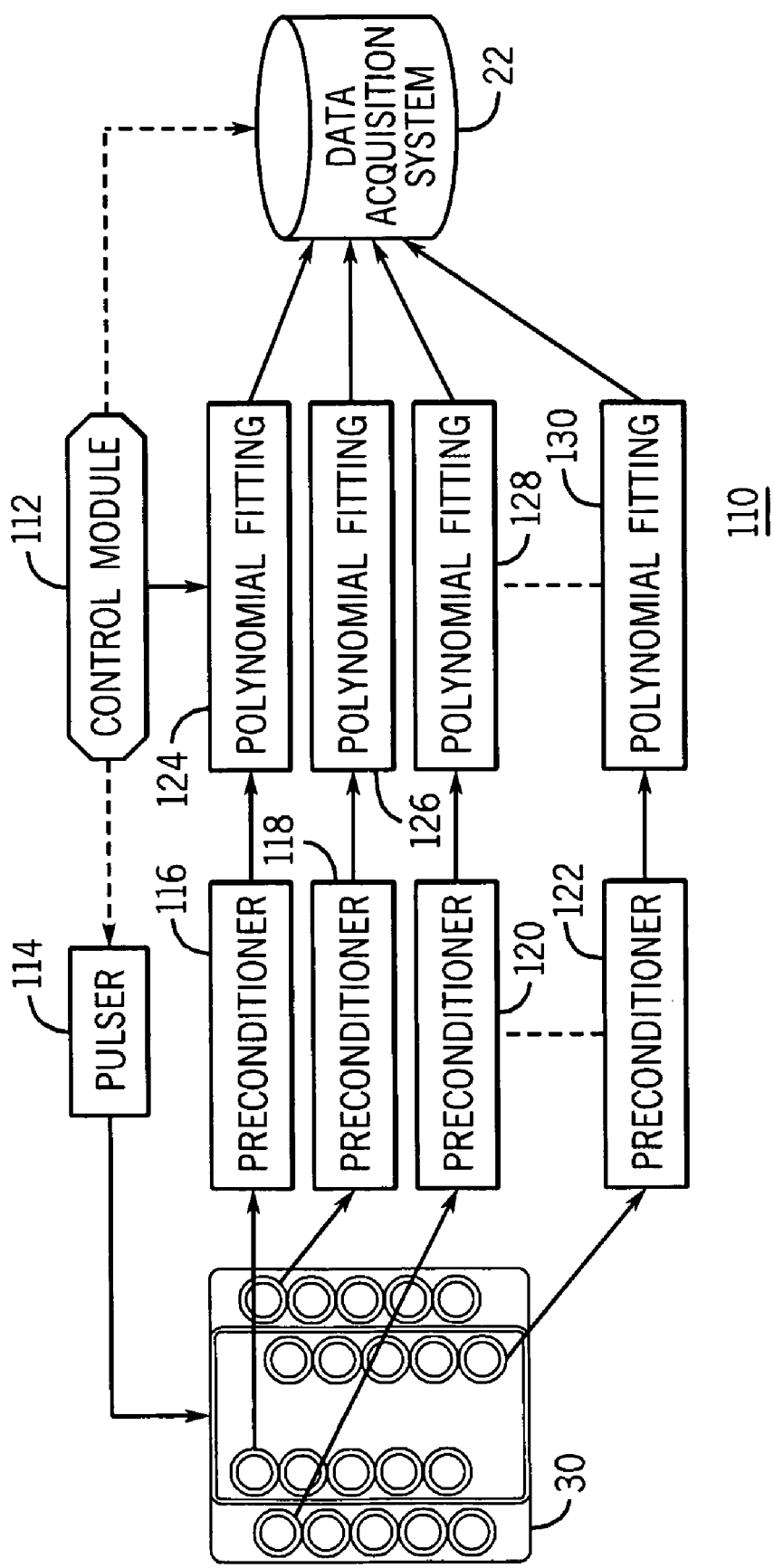
FIG. 6 is a block diagram of an exemplary embodiment of circuitry that may be used to process data obtained by a PIG according to an exemplary embodiment of the present invention.

FIG. 6 is a block diagram showing an exemplary embodiment of circuitry that may be used to process data obtained by the PIG 14. The diagram is generally referred to by the reference number 110. A control module 112 is adapted to control a pulser 114 to provide a PEC signal to an exemplary sensor sector 30. In the embodiment illustrated in FIG. 6, data from each of four linear sensor arrays on the sensor sector 30 is delivered to a respective pre-conditioner circuit 116, 118, 120 or 122. The pre-conditioner modules 116, 118, 120 and 122 perform preliminary filtration and amplitude limitation on the data. After being processed by the pre-conditioner circuits, data is delivered to respective polynomial fitting circuits 124, 126, 128 or 130. The processing algorithm employed by the polynomial fitting circuits 124, 126, 128 and 130 may operate to fit a polynomial curve to the pulsed eddy current response, allowing a determination of the polynomial coefficients explained above with reference to FIG. 5. The obtained coefficients are recorded for every sensor at each measuring point to an on-board data storage device such as the data acquisition system 22. By storing only the polynomial coefficients, the amount of data that is stored in the on-board storage device can be reduced in 50-100 times. Additional multiplexing during the data acquisition may be employed to reduce number of the data acquisition channels. Finally, the described algorithm includes a low pass filtration feature as a part of the curve fitting routine.

After inspection of the pipeline is completed, the data acquisition system 22 may be connected to a computer to retrieve the acquired data. If the data corresponds to parametric coefficients as described above, a transfer function is applied to the polynomial coefficients to compute wall thickness value at any inspected point. The coefficients of the obtained waveform are used to fit a non-linear transfer function relating the fit coefficients to the thickness, permeability, conductivity and lift-off of the test specimens from which the responses were measured. On subsequent inspections of the pipeline with unknown physical parameters, the measured pulsed eddy current response is parameterized and the previously computed transfer function is used to interpret the fit coefficients and estimate the physical parameters and sensor lift-off. Custom software may be developed to provide an appropriate transfer function for each sensor according to its position in a sensor sector and sensor stage. Two-dimensional eddy current images of the inspected pipeline surface may be constructed and analyzed. Conventional methods of image processing and analysis may be used to locate spots that have undesirable wall thinning. Repair procedures may be applied to those spots.

Figure 7:
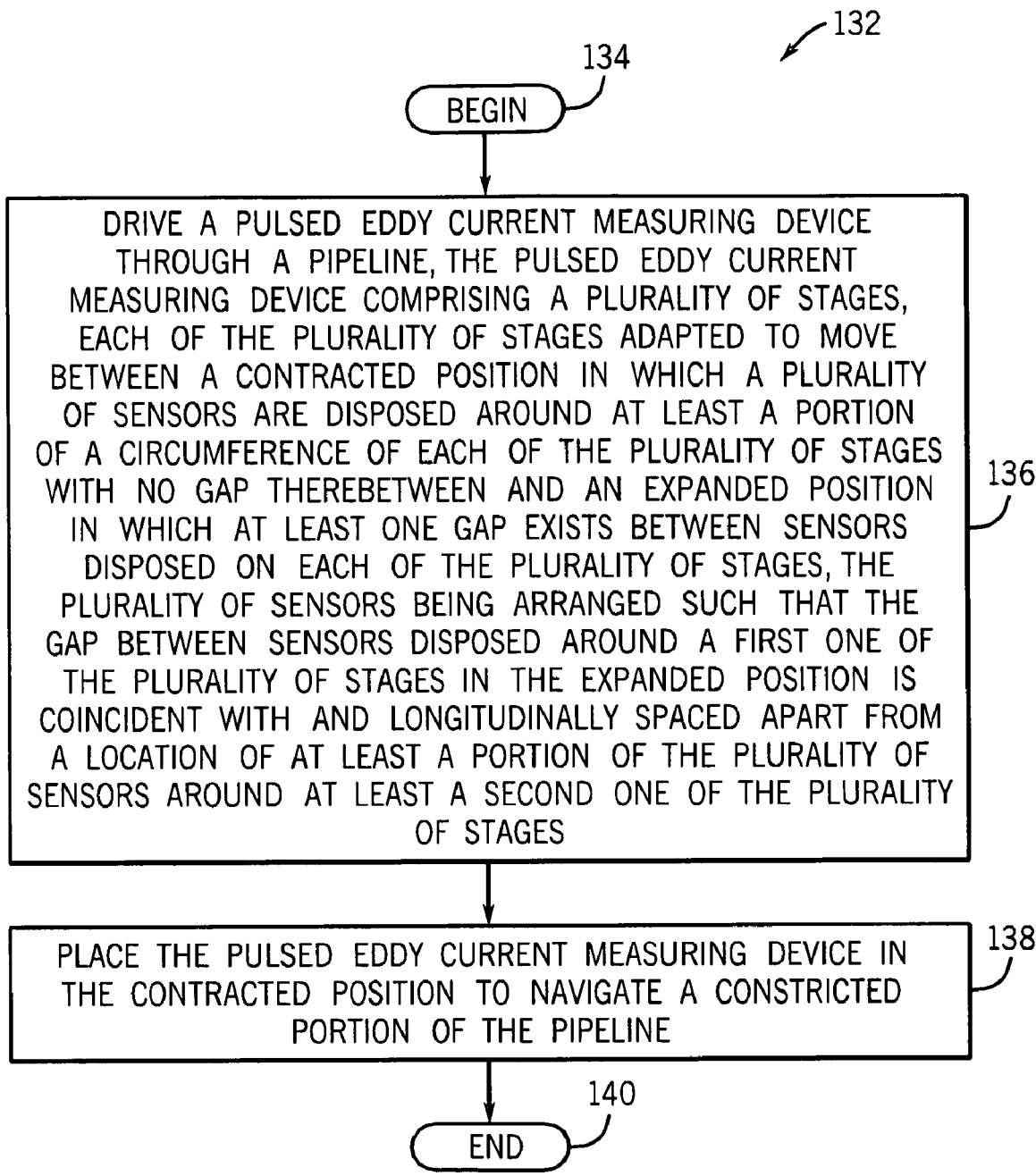
FIG. 7 is a flowchart showing exemplary steps for operating a PEC sensor according to an exemplary embodiment of the present invention.

FIG. 7 is a flowchart showing exemplary steps for operating a PEC sensor according to an exemplary embodiment of the present invention. The flowchart is generally referred to by the reference number 132. At block 134, the process begins. At block 136, a pulsed eddy current measuring device such as the PIG illustrated in FIG. 1 is driven through a pipeline. As described above, the pulsed eddy current measuring device comprises a plurality of stages. Each of the plurality of stages is adapted to move between a contracted position in which a plurality of sensors are disposed around at least a portion of a circumference of each of the plurality of stages with no gap therebetween and an expanded position in which at least one gap exists between sensors disposed on each of the plurality of stages. The plurality of sensors is arranged such that the gap between sensors disposed around a first one of the plurality of stages in the expanded position is coincident with and longitudinally spaced apart from a location of at least a portion of the plurality of sensors around at least second one of the plurality of stages.

At block 138, the pulsed eddy current measuring device is placed in the contracted position to facilitate navigation of a constricted portion of the pipeline. At black 140, the process ends.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A pulsed eddy current pipeline inspection device, comprising:
    a plurality of stages longitudinally spaced apart from each other and adapted to move between a contracted position and an expanded position; and
    a plurality of pulsed eddy current sensors disposed around at least a portion of a circumference of each of the plurality of stages in the contracted position with at least one gap between pulsed eddy current sensors in each of the plurality of stages in the expanded position, the plurality of pulsed eddy current sensors being arranged such that the at least one gap in a first one of the plurality of stages is aligned with a portion of a second one of the plurality of stages that has pulsed eddy current sensors disposed thereon, such that an entire circumference of a pipeline is covered by the plurality of pulsed eddy current sensors.

2. The pulsed eddy current pipeline inspection device recited in claim 1, wherein each of the plurality of stages comprises a plurality of sensor sectors.

3. The pulsed eddy current pipeline inspection device recited in claim 2, wherein a portion of the plurality of pulsed eddy current sensors are disposed in a linear array on each of the plurality of sensor sectors.

4. The pulsed eddy current pipeline inspection device recited in claim 1, comprising a control module that provides a signal to a pulser causing the pulser to deliver a pulsed eddy current input to a drive coil to excite at least a portion of the plurality of pulsed eddy current sensors.

5. The pulsed eddy current pipeline inspection device recited in claim 4, wherein the drive coil is positioned adjacent to at least a portion of the plurality of pulsed eddy current sensors.

6. The pulsed eddy current pipeline inspection device recited in claim 1, comprising a preconditioning circuit adapted to receive data from the plurality of pulsed eddy current sensors and to perform filtration and amplitude limitation on the data.

7. The pulsed eddy current pipeline inspection device recited in claim 1, comprising a polynomial fitting module adapted to receive data obtained by the plurality of pulsed eddy current sensors and to calculate at least one coefficient of a polynomial equation that approximates a waveform corresponding to the received data.

8. The pulsed eddy current pipeline inspection device recited in claim 7, comprising a data acquisition system that is adapted to store the at least one coefficient.

9. A pipeline inspection gage (PIG), comprising:
    a plurality of stages longitudinally spaced apart from each other and adapted to move between a contracted position and an expanded position;
    a plurality of pulsed eddy current sensors disposed around at least a portion of a circumference of each of the plurality of stages in the contracted position with at least one gap between pulsed eddy current sensors in each of the plurality of stages in the expanded position, the plurality of pulsed eddy current sensors being arranged such that the at least one gap in a first one of the plurality of stages is aligned with a portion of a second one of the plurality of stages that has pulsed eddy current sensors disposed thereon, such that an entire circumference of a pipeline is covered by the plurality of pulsed eddy current sensors;
    a data acquisition module that is adapted to receive data corresponding to a condition of a pipeline from the plurality of sensors; and
    a power supply that is adapted to supply power to the data acquisition module.

10. The PIG recited in claim 9, comprising a positional component adapted to determine a position of the PIG in the pipeline.

11. The PIG recited in claim 9, wherein each of the plurality of stages comprises a plurality of sensor sectors.

12. The PIG recited in claim 11, wherein a portion of the plurality of pulsed eddy current sensors are disposed in a linear array on each of the plurality of sensor sectors.

13. The PIG recited in claim 9, comprising a control module that provides a signal to a pulser causing the pulser to deliver a pulsed eddy current input to a drive coil to excite at least a portion of the plurality of pulsed eddy current sensors.

14. The PIG recited in claim 13, wherein the drive coil is positioned adjacent to at least a portion of the plurality of pulsed eddy current sensors.

15. The PIG recited in claim 9, comprising a preconditioning circuit adapted to receive data from the plurality of pulsed eddy current sensors and to perform filtration and amplitude limitation on the data.

16. The PIG recited in claim 9, comprising a polynomial fitting module adapted to receive data obtained by the plurality of pulsed eddy current sensors and to calculate at least one coefficient of a polynomial equation that approximates a waveform corresponding to the received data.

17. The PIG recited in claim 16, wherein the data acquisition system is adapted to store the at least one coefficient.

18. A method of evaluating a pipeline, comprising:
driving a pulsed eddy current measuring device through the pipeline, the pulsed eddy current measuring device comprising a plurality of stages, each of the plurality of stages adapted to move between a contracted position in which a plurality of pulsed eddy current sensors are disposed around at least a portion of a circumference of each of the plurality of stages with no gap therebetween and an expanded position in which at least one gap exists between sensors disposed on each of the plurality of stages, the plurality of pulsed eddy current sensors being arranged such that the gap between pulsed eddy current sensors disposed around a first one of the plurality of stages in the expanded position is coincident with and longitudinally spaced apart from a location of at least a portion of the plurality of pulsed eddy current sensors around at least a second one of the plurality of stages, such that an entire circumference of the pipeline is covered by the plurality of pulsed eddy current sensors; and placing the pulsed eddy current measuring device in the contracted position to navigate a constricted portion of the pipeline.

19. The method recited in claim 18, comprising providing a signal to a pulser causing the pulser to deliver a pulsed eddy current input to a drive coil to excite at least a portion of the plurality of pulsed eddy current sensors.

20. The method recited in claim 18, comprising:
receiving data from the plurality of pulsed eddy current sensors;
performing a filtration operation on the received data; and
performing an amplitude limitation operation on the received data.

21. The method recited in claim 18, comprising:
performing a polynomial fitting operation on data received from the plurality of pulsed eddy current sensors; and
calculating at least one coefficient of a polynomial equation that approximates a waveform corresponding to the received data.

22. The method recited in claim 21, comprising storing the at least one coefficient in a data acquisition module.

* * * * *

UNITED STATES PATENT AND TRADEMARK OFFICE
CERTIFICATE OF CORRECTION

PATENT NO. : 7,402,999 B2 Page 1 of 1
APPLICATION NO. : 11/290916
DATED : July 22, 2008
INVENTOR(S) : Plotnikov et al.

It is certified that error appears in the above-identified patent and that said Letters Patent is hereby corrected as shown below:

Title page on Page 2, in Item (56), under "FOREIGN PATENT DOCUMENTS", in Column 2, Line 3, delete "2219975 A" and insert -- 2291975 A --, therefor.

In Column 7, Line 47, after "least" insert -- a --.

In Column 7, Line 50, delete "black" and insert -- block --, therefor.

Signed and Sealed this

Seventeenth Day of March, 2009

JOHN DOLL
*Acting Director of the United States Patent and Trademark Office*